(12) United States Patent
Nakabayashi et al.

(10) Patent No.: US 9,169,482 B2
(45) Date of Patent: Oct. 27, 2015

(54) METHOD FOR SYNTHESIZING CDNA

(75) Inventors: Yuko Nakabayashi, Otsu (JP); Takashi Uemori, Otsu (JP); Hiroyuki Mukai, Otsu (JP); Kiyozo Asada, Otsu (JP)

(73) Assignee: TAKARA BIO INC., Otsu-Shi (JP)

(*) Notice: Subject to any disclaimer, the term of this patent is extended or adjusted under 35 U.S.C. 154(b) by 0 days.

(21) Appl. No.: 13/697,665

(22) PCT Filed: May 9, 2011

(86) PCT No.: PCT/JP2011/060643
§ 371 (c)(1),
(2), (4) Date: Nov. 13, 2012

(87) PCT Pub. No.: WO2011/142310
PCT Pub. Date: Nov. 17, 2011

(65) Prior Publication Data
US 2013/0065281 A1    Mar. 14, 2013

(30) Foreign Application Priority Data
May 14, 2010 (JP) .................................. 2010-111595

(51) Int. Cl.
*C12P 19/34* (2006.01)
*C12N 15/10* (2006.01)

(52) U.S. Cl.
CPC ............. *C12N 15/1096* (2013.01); *C12P 19/34* (2013.01)

(58) Field of Classification Search
None
See application file for complete search history.

(56) References Cited

U.S. PATENT DOCUMENTS

| | | | |
|---|---|---|---|
| 2005/0014169 A1* | 1/2005 | Latham et al. ................... | 435/6 |
| 2005/0053940 A1* | 3/2005 | Ikeda et al. ...................... | 435/6 |
| 2006/0223073 A1* | 10/2006 | Boyes et al. ...................... | 435/6 |
| 2010/0015602 A1 | 1/2010 | Korfhage et al. | |
| 2011/0020878 A1* | 1/2011 | Lanes et al. ................. | 435/91.2 |

FOREIGN PATENT DOCUMENTS

| | | | |
|---|---|---|---|
| EP | 1004676 A1 | 5/2000 | |
| EP | 1862545 A1 | 12/2007 | |
| JP | 2005-304396 A | 11/2005 | |
| JP | 2005304396 A | * 11/2005 | |
| JP | 2008-533997 A | 8/2008 | |
| WO | WO 99/09213 A1 | 2/1999 | |
| WO | WO 2006/103039 A1 | 10/2006 | |

OTHER PUBLICATIONS

Chen et al. (Use of bacterially-expressed antigen for detection of antibodies to the EBV-specific deoxyribonuclease in sera from patients with nasopharyngeal carcinoma, Journal of Virogical Methods, vol. 45, pp. 49-66).*
Hanaki et al. (DNase I Activity Retained after Heat Inactivation in Standard Buffer, BioTechniques 29:38-42 (Jul. 2000)).*
Life Technologies (DNase I Demystified, attached, 2001).*
Chen et al. (Use of bacterially-expressed antigen for detection of antibodies to the EBV-specific deoxyribonuclease in sera from patients with nasopharyngeal carcinoma, Journal of Virological Methods, 45 (1993) 49-66).*
DNAse Inhibition for Perfect DNA Isolations (hereinafter "DNase Inhibition"; attached, 2005).*
Anisimova et al. (Thermolabile duplex-specific nuclease, Biotechnol Lett (2009) 31:251-257, Sep. 23, 2008).*
Chen, et al., "Use of bacterially-expressed antigen for detection of antibodies to the EBV-specific deoxyribonuclease in sera from patients with nasopharyngeal carcinoma," Journal of Virological Methods, 1993, vol. 45, pp. 49-66.
International Search Report for International Application No. PCT/JP2011/060643 dated Jun. 7, 2011.
Silkie et al., "Reagent decontamination to eliminate false-positives in *Escherichia coli* qPRC," Journal of Microbiological Methods, 2008, vol. 72, pp. 275-282.
Extended European Search Report, dated Feb. 3, 2014, for European Application No. 11780567.1.
Liu et al., "Protection of Megabase-Sized Chromosomal DNA from Breakage by DNase Activity in Plant Nuclei," BioTechniques, vol. 26, No. 2, Feb. 1999, pp. 258-261, XP002718913.
Sigma-Aldrich, "Product Information—Deoxyribonuclease I bovine, recombinant expressed in a proprietary host," Catalog No. D7691, Jan. 30, 2008, XP002718934.

\* cited by examiner

*Primary Examiner* — Christopher M Babic
*Assistant Examiner* — Aaron Priest
(74) *Attorney, Agent, or Firm* — Birch, Stewart, Kolasch & Birch, LLP (57) ABSTRACT

A method for synthesizing cDNA characterized by preparing a reaction solution that does not allow an endodeoxyribonuclease to show its activity, without thermal deactivation of the endodeoxyribonuclease or removal of the endodeoxyribonuclease, and carrying out a reverse transcription reaction, wherein the reaction solution contains a treated sample and a reverse transcriptase, the treated sample being formed by treating a sample comprising RNA and DNA with the endodeoxyribonuclease to degrade DNA in the sample. The method and the kit for synthesizing cDNA of the present invention are widely useful in genetic engineering fields.

11 Claims, 1 Drawing Sheet

METHOD FOR SYNTHESIZING CDNA

TECHNICAL FIELD

The present invention relates to a method useful for synthesizing cDNA and a kit useful for synthesizing cDNA.

BACKGROUND ART

In order to elucidate life phenomena, it is very important to analyze mRNA molecules of diversified genes. By the finding of an RNA-dependent DNA polymerase, in other words a reverse transcriptase, it is made possible to carry out a reverse transcription reaction for synthesizing cDNA with RNA as a template, thereby making remarkable advancements in the method of analyzing mRNA molecules. The method of analyzing mRNA molecules using a reverse transcriptase now has become an essential experimental method in studies concerning genes. PCR method for amplifying DNA fragments with cDNA synthesized by a reverse transcription reaction as a template is referred to as RT-PCR method. The RT-PCR method is utilized in cloning of cDNA derived from mRNA or in the production of cDNA libraries, and also is useful as a method for examining an expression state of a particular RNA.

However, in a case where DNA is contaminated in a sample used in cDNA synthesis, a region on DNA encoding RNA or a pseudogene may be amplified, thereby making it difficult to selectively obtain only the DNA synthesized with RNA as a template. In order to inhibit the production of an amplified product derived from DNA contaminated in the sample, a method in which a nucleotide analog and a compound which lowers a Tm value are used during a reverse transcription reaction (Patent Publication 1), a method including degrading DNA in the sample with an endodeoxyribonuclease (hereinafter, may be referred to as endoDNase) such as deoxyribonuclease I (hereinafter, may be referred to as DNaseI), and thereafter carrying out a reverse transcription reaction, and the like are employed.

In a case where a reverse transcription reaction is carried out after degrading DNA in the sample with DNaseI, in order to inhibit the degradation of cDNA, the DNaseI is generally inactivated or removed prior to the reverse transcription reaction, by a heat treatment, a phenol/chloroform extraction or the like. However, it has been known that the phenol/chloroform extraction is complicated, and that a heat treatment in the presence of divalent metal ions which are essential for the reaction of DNaseI leads to hydrolysis of RNA. Although a method of actions with DNaseI and a reverse transcriptase at the same time is also proposed (Patent Publications 2 and 3), DNaseI would also degrade DNA in a DNA/RNA hybrid, so that the cDNA synthesized by a reverse transcription reaction in this manner is subjected to degradation with DNaseI.

PRIOR ART PUBLICATIONS

Patent Publications

Patent Publication 1: WO 99/09213
Patent Publication 2: Japanese Patent Laid-Open No. 2005-304396
Patent Publication 3: WO 2006/103039

SUMMARY OF THE INVENTION

Problems to be Solved by the Invention

The problems to be solved by the present invention are to provide a method for synthesizing cDNA capable of simply and conveniently inhibit the production of amplified products derived from DNA contaminated in a sample.

Means to Solve the Problems

The present inventors have found that a reaction solution composition in which endoDNase does not show activity and a reverse transcriptase shows activity can be prepared, and further the present invention relating to a method for synthesizing cDNA and a kit for synthesizing cDNA which can solve the above problems has been perfected, based on the findings.

Concretely, the present invention relates to:
[1] a method for synthesizing cDNA characterized by preparing a reaction solution that does not allow an endodeoxyribonuclease to show its activity, without thermal deactivation of the endodeoxyribonuclease or removal of the endodeoxyribonuclease, and carrying out a reverse transcription reaction,
wherein the reaction solution contains a treated sample and a reverse transcriptase, the treated sample being formed by treating a sample comprising RNA and DNA with the endodeoxyribonuclease to degrade DNA in the sample;
[2] the method according to [1], wherein the method includes the following steps (a) to (c):
(a) obtaining a composition containing a sample containing RNA and DNA, and the endodeoxyribonuclease;
(b) treating the composition obtained in step (a) under conditions sufficient to degrade DNA in the sample with the endodeoxyribonuclease; and
(c) adding an additive and a reverse transcriptase to the composition treated in step (b) to prepare a reaction solution that does not allow the endodeoxyribonuclease to show its activity, and carrying out a reverse transcription reaction by the reverse transcriptase;
[3] the method according to [1], wherein the endodeoxyribonuclease is a deoxyribonuclease I;
[4] the method according to [1], wherein the reverse transcriptase is a reverse transcriptase derived from Moloney murine leukemia virus;
[5] the method according to [2], wherein the additive is at least one member selected from the group consisting of a reducing agent, a monovalent cation and salts thereof;
[6] The method according to [5], wherein the monovalent cation is an ammonium ion;
[7] a method of amplifying cDNA, including the step of carrying out a gene amplification method with the cDNA synthesized according to the method as defined in any one of [1] to [6] as a template; and
[8] a kit for use in the method as defined in any one of [1] to [7], containing (A) an endodeoxyribonuclease, (B) a buffering agent, (C) a reverse transcriptase, and (D) an additive for preparing a composition for a reverse transcription reaction that allows the reverse transcriptase to show its activity and does not allow the endodeoxyribonuclease to show its activity.

Effects of the Invention

According to the present invention, the synthesis for cDNA excellent in operability, quantification or the like is made possible, the synthesis which is capable of inhibiting the production of an amplified product derived from DNA contaminated in a sample and.

MODES FOR CARRYING OUT THE INVENTION

The method for synthesizing cDNA of the present invention is characterized by preparing a reaction solution that does not allow an endodeoxyribonuclease to show its activity, without thermal deactivation of the endodeoxyribonuclease or removal of the endodeoxyribonuclease, and carrying out a reverse transcription reaction, wherein the reaction solution contains a treated sample and a reverse transcriptase, the treated sample being formed by treating a sample comprising RNA and DNA with the endodeoxyribonuclease to degrade DNA in the sample.

Conventionally, in a method including degrading DNA in a sample with an endoDNase, and then carrying out a reverse transcription reaction, it is required to, prior to the reverse transcription reaction, thermally deactivate the endoDNase or to remove the endoDNase, but the method of the present invention does not necessitate these procedures. In other words, according to the present invention, it is not required to carry out a heat treatment at 60° C. or higher or a separation procedure of a specified component between the degradation of DNA in a sample with an endoDNase and the reverse transcription reaction. Accordingly, in the present specification, the phrase "thermal deactivation of an endodeoxyribonuclease (endoDNase)" refers to a heat treatment of a sample containing the endoDNase at 60° C. or higher, the phrase "removal of endodeoxyribonuclease (endoDNase)" refers to a separation of the endoDNase from a sample containing endoDNase, and the phrase "without thermal deactivation of an endodeoxyribonuclease or removal of an endodeoxyribonuclease" means that the procedures mentioned above are not carried out.

The sample used in the method of the present invention, but not particularly limiting the present invention thereto, may be a sample containing RNA, and includes, for example, a sample containing RNA and DNA. Concretely, the sample includes living body-derived samples such as cells, tissues or blood; a nucleic acid-containing sample obtained by treating the samples by means of a well known method; and samples possibly containing an organism such as foods, soils or wastewaters. An example of a nucleic acid-containing sample obtained by treating a living body-derived sample by means of a well known method includes, for example, samples obtained from cell disruptions or those obtained by fractionation thereof; samples enriched with total RNA in the sample, or particular RNA molecules, for example, those enriched with mRNA, or the like, and the samples may be samples contaminated with DNA.

In the present specification, the endodeoxyribonuclease (endoDNase) refers to an enzyme which cleaves DNA strand in endo form. The endoDNase usable in the present invention preferably includes double-stranded DNA specific endoDNase, and more preferably includes, for example, a sequence-nonspecific endonuclease such as DNaseI or Shrimp DNase, or a sequence-specific endonuclease such as a restriction enzyme.

The treated sample in which DNA in the sample is degraded with an endoDNase is not particularly limited, as long as the sample is kept under conditions such that DNA in the sample is degraded with an endoDNase, and one of ordinary skill in the art would be able to appropriately prepare the sample depending upon endoDNase or the sample. Although not particularly limiting the present invention thereto, in a case where DNaseI is used as an endoDNase, the keeping conditions are conditions including preferably at 20° to 45° C. for 10 seconds to 12 hours, more preferably at 25° to 44° C. for 30 seconds to 1 hour, and even more preferably at 30° to 43° C. for 1 minute to 30 minutes.

The reverse transcriptase usable in the present invention may be an enzyme which possesses reverse transcription activity, in other words activity for synthesizing, with RNA as a template, DNA complementary thereto, and the reverse transcriptase includes, for example, reverse transcriptases derived from viruses, such as reverse transcriptase derived from Moloney murine leukemia virus (MMLV-derived reverse transcriptase) and reverse transcriptase derived from avian myeloblastosis virus (AMV-derived reverse transcriptase); reverse transcriptases derived from eubacteria such as DNA polymerase derived from thermophilic bacteria belonging to the genus *Bacillus* (Bca DNA polymerase or the like), and DNA polymerase which possesses both reverse transcription activity and DNA-dependent DNA polymerase activity derived from bacteria belonging to the genus *Thermus* (Tth DNA polymerase or the like). In the present invention, the reverse transcriptases derived from viruses are preferably used, and the MMLV-derived reverse transcriptase is more preferably used. In addition, either a naturally occurring enzyme or a recombinant enzyme can be used as the reverse transcriptase in the present invention, and a reverse transcriptase of which naturally occurring amino acid sequence is subjected to modification within the range that the reverse transcriptase possesses reverse transcription activity also can be used.

In the present specification, the phrase "a reaction solution that does not allow the endodeoxyribonuclease to show its activity" means "a reaction solution in which the endodeoxyribonuclease does not show DNA degradation activity." The reaction solution refers to, for example, a reaction solution of which absorbance at 260 nm does not substantially change even when the reaction solution containing 40 µg/mL bovine thymus DNA is kept at 25° C. for 10 minutes in the presence of 8 U/mL DNaseI (TAKARA BIO INC.), a titer as indicated on a manufactured article.

The reaction solution that allow the endoDNase does not show its activity contains the treated sample and the reverse transcriptase, can be prepared by, for example, adding an additive, a reverse transcriptase and other components to the reaction solution after the degradation of DNA in the sample with the endoDNase to make a composition in which the endoDNase does not show DNA degradation activity. In other words, a method including (a) obtaining a composition containing a sample and an endodeoxyribonuclease; (b) treating the composition obtained in step (a) under conditions sufficient to degrade DNA in the sample with the endodeoxyribonuclease; and (c) adding an additive and a reverse transcriptase to the composition treated in step (b) to prepare a reaction solution that does not allow the endodeoxyribonuclease to show its activity, and carrying out a reverse transcription reaction is one preferred embodiment of the method of the present invention.

It is preferable that the composition containing the sample and the endodeoxyribonuclease in the above step (a) further contains a buffering agent such as Tris-HCl, divalent metal ions such as magnesium ions or manganese ions, and a reducing agent such as dithiothreitol (hereinafter, may be referred to as DTT). The kinds or the concentration of the buffering agent, the divalent metal ions and the reducing agent can be properly selected within the range that shows activity of degrading DNA in the sample in the next step (b) with the endoDNase, based on enzymological properties such as reaction properties or stability of the endoDNase or experimentations. It is preferable to set the kinds or the concentration so that the endoDNase shows high activity and shows high stability. For example, in a case where DNaseI is used as the endoDNase, the kinds or the concentration of the buffering agent may be set so that the addition thereof gives near an optimal pH of the endoDNase, and the kinds or the concentration which is capable of adjusting a pH of the reaction solution to a range of from 5 to 10 is preferable. In addition, the kinds or the concentration of the reducing agent may be set such that the endoDNase show high stability; for example, in a case where DNaseI is used as the endoDNase, it is preferable that the composition contains DTT in a concentration of 1 mM or more, and less than 5 mM.

The conditions sufficient to degrade DNA in the sample with the endodeoxyribonuclease in the above step (b) are not particularly limited, as long as the conditions of temperature and time are those at which the degradation of DNA is carried out so that the product derived from the DNA in the sample cannot be substantially confirmed, and one of ordinary skill in the art can properly set the conditions depending on the endoDNase or the sample. Although not particularly limiting the present invention thereto, in a case where DNaseI is used as the endoDNase, conditions of at 20° to 45° C. for 10 seconds to 12 hours are preferably exemplified, conditions of at 25° to 44° C. for 30 seconds to 1 hour are more preferably exemplified, and conditions of at 30° to 43° C. for 1 minute to 30 minutes are even more preferably exemplified.

The additive in the above step (c) includes at least one member selected from the group consisting of a reducing agent, a monovalent cation and salts thereof. The additive can be used in the present invention, for example, in the form of an aqueous solution containing the additive, preferably a buffer containing the additive. The kinds or the concentration of the buffering agent used in the above buffer is not particularly limited, as long as the reaction solution can be adjusted to a desired pH, and the kinds or the concentration capable of changing a pH of the reaction solution to near an optimal pH of the reverse transcriptase usable in a reverse transcription reaction by addition thereof is preferred. Although not particularly limiting the present invention thereto, the above buffering agent includes Good's buffers such as Tris-HCl. The above reducing agent includes, for example, a thiol reducing agent such as DTT, or 2-mercaptoethanol. In addition, the above monovalent cations include ammonium ions, and alkali metal ions such as potassium ions, lithium ions and sodium ions, and salts thereof, for example, ammonium sulfate or potassium chloride may be used. The kinds or the amount used of the reducing agent, the monovalent cations or salts thereof is not particularly limited, as long as the endoDNase does not show its activity and the reverse transcriptase effectively functions in a composition to which the additive, and one of ordinary skill in the art would be able to properly decide depending on the disclosure of the present specification. Although not particularly limiting the present invention thereto, the component contained in the composition in which the endoDNase does not show its activity and the reverse transcriptase effectively functions, in a case where the endoDNase is DNaseI, includes, for example, ammonium sulfate, DTT and potassium chloride. The concentration of ammonium sulfate in the composition preferably includes 5 mM or more, more preferably includes from 10 to 30 mM, and even more preferably includes from 14 to 28 mM. In addition, the concentration of DTT preferably includes 5 mM or more, more preferably includes from 11 to 30 mM, and even more preferably includes from 12 to 20 mM. In addition, the concentration of potassium chloride preferably includes 1 mM or more, more preferably includes from 3 to 30 mM, and even more preferably includes from 5 to 20 mM. Concretely, as the final concentration in the composition the above additive is blended such that the composition preferably contains 5 mM or more of ammonium sulfate, 5 mM or more of DTT and 1 mM or more potassium chloride, more preferably contains 10 to 30 mM ammonium sulfate, 11 to 30 mM DTT and 3 to 30 mM potassium chloride, even more preferably contains 14 to 28 mM ammonium sulfate, 11 to 30 mM DTT and 5 to 20 mM potassium chloride, and even more preferably contains 14 to 28 mM ammonium sulfate, 12 to 20 mM DTT and 5 to 20 mM potassium chloride.

In addition, the above additive can be used in the form of a buffer for preparing a reverse transcription reaction solution prepared by mixing components necessary for a reverse transcription reaction such as a reverse transcriptase, a buffering agent, an oligonucleotide primer and dNTP. Taking into consideration the procedures and stability of the reverse transcriptase, an embodiment where the buffer contains a component necessary for a reverse transcription reaction other than the reverse transcriptase, and only the reverse transcriptase is separately added thereto is preferred.

The conditions of the reverse transcription reaction are not particularly limited, as long as the conditions are sufficient to synthesize a primer extension strand complementary to a template RNA. The conditions sufficient to synthesize the primer extension strand complementary to the template RNA is not particularly limited, and the temperature conditions are preferably from 25° to 60° C., and more preferably from 30° to 50° C. In addition, the reaction time is preferably from 5 to 120 minutes, and more preferably from 15 to 60 minutes. In addition, after the reverse transcription reaction, the reaction solution may be incubated under the conditions which inactivate the reverse transcriptase. The conditions for inactivating the reverse transcriptase include, for example, conditions of 85° C. for 5 seconds.

The method for amplifying cDNA of the present invention includes the step of carrying out a gene amplification reaction with the cDNA synthesized according to the method for synthesizing cDNA of the present invention as a template. In the nucleic acid amplification with the cDNA as a template, a well known gene amplification method in the art such as PCR method, ICAN method, LAMP method, or SDA method can be utilized. For example, in a case where PCR method is used in the nucleic acid amplification, general conditions for PCR can be applied, the amplification is carried out by, for example, a reaction comprising three steps of dissociating double-stranded template DNA to single strand (denaturation), annealing a primer to the single-stranded template DNA and synthesizing a complementary strand from the primer (extension), or a reaction comprising a two-step reaction, in which among the three-step reaction mentioned above, the annealing and the extension of the primer are carried out at the same temperature, referred to as "shuttle PCR" ["*PCR Ho Saizensen (Front Line of PCR Method)*," "(*Tanpakushitsu Kakusan Koso (Proteins, Nucleic Acids and Enzymes)*" Supplement, 41(5), 425 to 428 (1996)]. As PCR method, real-time PCR capable of monitoring nucleic acid amplification with an intercalating dye, a FRET-labeled probe or the like can be utilized.

The kit of the present invention is a kit for use in the method for synthesizing cDNA of the present invention or the method for amplifying cDNA of the present invention, and the kit contains (A) an endodeoxyribonuclease, (B) a buffering agent, (C) a reverse transcriptase, and (D) an additive for preparing a composition for a reverse transcription reaction that allows the reverse transcriptase to show its activity and does not allow the endodeoxyribonuclease to show its activity. The above buffering agent (B) may contain divalent metal ions and the like necessary for the reaction of endoDNase. In addition, the additive (D) may contain oligonucleotide primer or dNTP necessary for the reverse transcription reaction with the reverse transcriptase.

EXAMPLES

The present invention will be specifically described hereinbelow by the Examples, without intending to limit the scope of the present invention thereto.

Example 1

Study-1 of Reaction Composition for Inhibiting EndoDNase Activity

Five kinds of 20 μL-reaction solutions (Reaction Solutions 1 to 5) containing 5 U DNaseI [Recombinant DNaseI (RNase-free), TAKARA BIO INC.], 200 ng mouse genomic DNA, and the components as listed in Table 1 were prepared. In addition, five kinds of 20 μL-reaction solutions having the same compositions as mentioned above except that DNaseI was not contained were prepared. Here, Reaction Solution 1 is set so that each component has a concentration which is a half that of a standard reaction solution composition of DNaseI, and Reaction Solution 2 is set to have a pH near an optimal pH of the reverse transcriptase and contains dNTP, serving as a substrate of the reverse transcriptase. These reaction solutions were incubated at 37° C. for 15 minutes, and thereafter incubated at 85° C. for 5 seconds. Next, the amount of genomic DNA remaining in each of the reaction solutions was quantified according to real-time PCR in which Rsp18 gene region was used as a targeting sequence. Here, in the real-time PCR, SYBR Premix ExTaq (Perfect Real Time, TAKARA BIO INC.) was used, and a primer consisting of the nucleotide sequence as shown in SEQ ID NO: 1 of Sequence Listing and a primer consisting of the nucleotide sequence as shown in SEQ ID NO: 2 of Sequence Listing were used as a primer pair.

TABLE 1

| | Reaction Solution 1 | Reaction Solution 2 | Reaction Solution 3 | Reaction Solution 4 | Reaction Solution 5 |
|---|---|---|---|---|---|
| Tris-HCl (pH 7.5) | 20 | 20 | 20 | 20 | 20 |
| MgCl$_2$ | 4 | 4 | 4 | 4 | 4 |
| DTT | 2.5 | 2.5 | 2.5 | 2.5 | 12.5 |
| Tris-HCl (pH 9.2) | — | 50 | 50 | 50 | 50 |
| KCl | — | — | 10 | — | — |
| (NH$_4$)$_2$SO$_4$ | — | — | — | 14 | — |
| dNTP | — | 0.5 | 0.5 | 0.5 | 0.5 |

Concentration (mM)

The quantification results of genomic DNA according to the real-time PCR and the inhibition rate of degradation of genomic DNA in each of the reaction solution compositions are shown in Table 2. As shown in Table 2, contrary to Reaction Solution 1 in which genomic DNA in the reaction solution was completely degraded, the inhibition effects of degradation of DNA were found in Reaction Solutions 3 to 5, which were the reaction solution to which KCl or (NH$_4$)$_2$SO$_4$ was added, or the reaction solution in which the concentration of DTT was increased. In particular, high-inhibition effects of DNA degradation were found in Reaction Solution 4 to which (NH$_4$)$_2$SO$_4$ was added and Reaction Solution 5 in which the concentration of DTT was increased. Here, the inhibition rate of degradation was calculated according to the following formula:

Inhibition Rate(%)=Amount of DNA in Reaction Solution Containing DNaseI/Amount of DNA in Reaction Solution Not Containing DNaseI×100

TABLE 2

| | Reaction Solution 1 | Reaction Solution 2 | Reaction Solution 3 | Reaction Solution 4 | Reaction Solution 5 |
|---|---|---|---|---|---|
| DNaseI(−) | 216 ng | 152 ng | 188 ng | 163 ng | 140 ng |
| DNaseI(+) | 0 g | 2.97 ng | 5.43 ng | 116 ng | 119 ng |
| Inhibition Rate | 0% | 2% | 3% | 71% | 85% |

Example 2

Study-2 of Reaction Composition for Inhibiting EndoDNase Activity

In order to construct a reaction composition completely inhibiting endoDNase activity, six kinds of 20 μL-reaction solutions (Reaction Solutions 1 to 6) containing 5 U DNaseI (TAKARA BIO INC.), 200 ng mouse genomic DNA, and the components as listed in Table 3 were prepared. In addition, six kinds of 20 μL-reaction solutions having the same compositions except that DNaseI was not contained were prepared. These reaction solutions were incubated at 37° C. for 15 minutes, and thereafter incubated at 85° C. for 5 seconds. Next, each of the reaction solutions was subjected to agarose gel electrophoresis, thereby confirming degradation of mouse genomic DNA with DNaseI.

TABLE 3

| | Reaction Solution 1 | Reaction Solution 2 | Reaction Solution 3 | Reaction Solution 4 | Reaction Solution 5 | Reaction Solution 6 |
|---|---|---|---|---|---|---|
| Tris-HCl (pH 7.5) | 40 | 20 | 20 | 20 | 10 | 10 |
| MgCl$_2$ | 8 | 4 | 4 | 4 | 2 | 2 |
| DTT | 5 | 2.5 | 12.5 | 12.5 | 11.25 | 11.25 |
| Tris-HCl (pH 9.2) | — | — | 50 | 50 | 50 | 50 |
| KCl | — | — | 10 | 10 | 10 | 10 |
| (NH$_4$)$_2$SO$_4$ | — | — | 14 | 28 | 14 | 28 |
| dNTP | — | — | 0.5 | 0.5 | 0.5 | 0.5 |

Concentration (mM)

Figure 1:
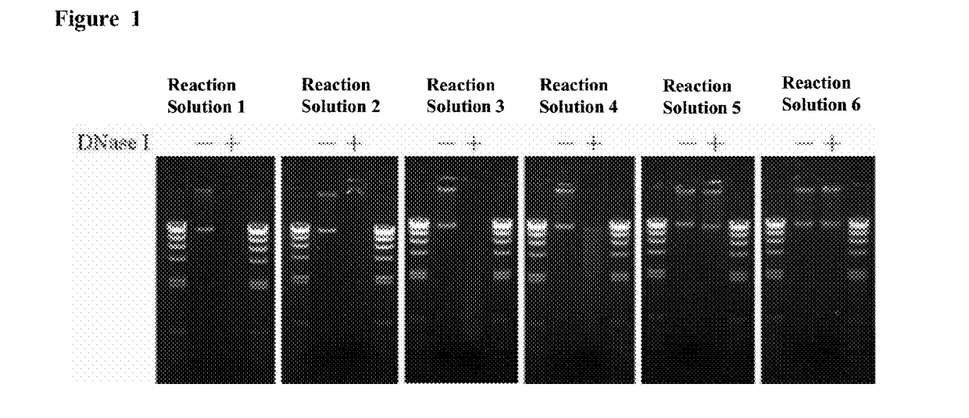
FIG. 1 is diagrams showing the results of agarose gel electrophoresis in Example 2.

The electrophoretic results are shown in FIG. 1. As shown in FIG. 1, in the compositions of Reaction Solutions 1 and 2, the bands of genomic DNA completely disappeared by the action of DNaseI. On the other hand, in the compositions of Reaction Solutions 3 and 4, the bands of genomic DNA did not completely disappear in the presence of DNaseI and a smeared electrophoretic image could be confirmed. It could be confirmed from this matter that DNaseI activity was inhibited in Reaction Solutions 3 and 4. In addition, since the extent of the inhibition was greater in Reaction Solution 4, it could be confirmed that (NH$_4$)$_2$SO$_4$ inhibited DNaseI activity in a concentration-dependent manner. Further, in the compositions of Reaction Solutions 5 and 6, the bands of genomic DNA did not change at all even in the presence of DNaseI, so that it could be confirmed that DNaseI activity was completely inhibited in these reaction solutions. It is shown from this matter that adjustment of the Mg concentration can further inhibit DNaseI activity other than the addition of KCl and $(NH_4)_2SO_4$ or an increase in the DTT concentration. It is suggested from the above results that it is made possible to carry out another enzyme reaction without action of DNaseI by, for example, degrading DNA with DNaseI in the composition of Reaction Solution 1, and adding an additive which is separately prepared so as to have a final concentration thereof to be the composition of Reaction Solution 5 or 6.

Example 3

Confirmation of DNase Activity

DNase activity of DNaseI was measured in a reaction solution having the components as listed in Reaction Solution 2 of Table 3 of Example 2 of which degradation of genomic DNA with DNaseI was confirmed, and in a reaction solution having the components as listed in Reaction Solution 5 of Table 3 of Example 2 of which degradation of genomic DNA was not found. Here, the activity unit of DNase shown hereinafter is such that an amount of the enzyme which increases absorbance with OD 260 of a reaction solution by 0.001 in 1 minute with bovine thymus DNA as a substrate is defined as 1 U.

Firstly, a solution having a total volume of 1 mL, containing the components as listed in Reaction Solution 2 or 5 of Table 3, 100 μL of a 60-fold dilution of DNaseI (TAKARA BIO INC., titer as indicated on a manufactured article=5 U/μL), and 40 μg bovine thymus DNA was prepared, and the absorbance (with OD 260) of the solution was measured every minute, while keeping the solution at 25° C. for 10 minutes. As a result, the reaction solution having the components as listed in Reaction Solution 2 of Table 3 was found to have activity of 39 U, per μL of DNaseI (titer as indicated on a manufactured article=5 U/μL) before the dilution. On the other hand, a change in absorbance was not found in the components as listed in Reaction Solution 5 of Table 3.

Next, the absorbance (OD 260) of a 1-mL solution containing the components as listed in Reaction Solution 5 of Table 3, 50 μL DNaseI (5 U/μL), and 40 μg bovine thymus DNA was measured every minute while keeping the solution at 25° C. for 10 minutes. As a result, a change in absorbance was not found in the reaction solution having the components as listed in Reaction Solution 5 of Table 3.

As described above, the reaction solution having the components as listed in Reaction Solution 2 of Table 3 showed activity of about 8 folds, as compared to the titer as indicated on the manufactured article. On the other hand, the reaction solution having the components as listed in Reaction Solution 5 of Table 3 had activity that was below the detection limit even when DNaseI was used in an amount of 30 folds that used upon the measurement of activity of the reaction solution having the components as listed in Reaction Solution 2 of Table 3. It could be confirmed from the above that the activity of DNaseI was completely inhibited in the reaction solution having the components as listed in Reaction Solution 5 of Table 3.

Example 4

Reverse Transcription Reaction-1 in the Presence of DNaseI in Reaction Composition, DNaseI Showing no Action In a reaction solution having the components as listed in Reaction Solution of Table 3 of Example 2 and a reaction solution having the components as listed in Reaction Solution 6 of Table 3 of Example 2, in a case where a reverse transcription reaction was carried out with a reverse transcriptase, the influences of DNaseI in the reaction solutions in the cDNA synthesis were verified by the following method.

A mixed solution having a total volume of 10 μL, containing a 1 μL-mouse liver total RNA solution serially diluted from 2 μg/μL to 20 μg/μL 10 U RNase Inhibitor (TAKARA BIO INC.), the components as listed in Reaction Solution 2 of Table 3, and 5 U DNaseI was prepared. In addition, a 10 μL-mixed solution having the same composition as the above except that DNaseI was not contained was prepared. These mixed solutions were incubated at 42° C. for 2 minutes, and thereafter a solution containing 200 U PrimeScript(registered trademark) RTase (TAKARA BIO INC), 20 U RNase Inhibitor (TAKARA BIO INC.), 100 mM Tris-HCl (pH 9.2) containing 50 pmol Oligo dT primer and 100 pmol Random 6 mers, 20 mM KCl, 20 mM DTT, 1 mM dNTP, or 28 mM or 56 mM $(NH_4)_2SO_4$ was respectively added thereto in an amount of 10 μL each, while mixing. In other words, the above solution containing a reverse transcriptase was added to the mixed solution after the DNase treatment, so as to have final concentrations of components other than the reverse transcriptase, DNaseI, the RNase inhibitor and the primers to be those components as listed in Reaction Solution 5 of Table 3, or the components as listed in Reaction Solution 6 of Table 3. Next, a reverse transcription reaction was carried out under the conditions of 37° C. for 15 minutes, and thereafter the reverse transcriptase was deactivated under the conditions of 85° C. for 5 seconds. The amount of cDNA synthesized after the reverse transcription reaction was evaluated by real-time PCR in which Rsp18 gene region was used as a targeting sequence. Here, in the real-time PCR, SYBR Premix ExTaq (Perfect Real Time, TAKARA BIO INC.) was used, and a primer consisting of the nucleotide sequence as shown in SEQ ID NO: 1 of Sequence Listing and a primer consisting of the nucleotide sequence as shown in SEQ ID NO: 2 of Sequence Listing were used as a primer pair.

The results of the real-time PCR are shown in Table 4. As shown in Table 4, there were no differences in Ct values, by the presence or absence of DNaseI. It could be confirmed from the results that DNaseI did not influence the cDNA synthesis with the reverse transcriptase in the reaction solution having components listed in Reaction Solution 5 of Table 3 and the reaction solution having components listed in Reaction Solution 6 of Table 3.

TABLE 4

| RNA/20 μL Reaction Solution | Reaction Solution 5 | | Reaction Solution 6 | |
|---|---|---|---|---|
| | DNase (−) | DNase (+) | DNase (−) | DNase (+) |
| NTC | — | — | — | — |
| 20 pg | 34.27 | 34.86 | 35.07 | 34.81 |
| 200 pg | 30.91 | 30.78 | 31.17 | 31.00 |
| 2 ng | 27.14 | 27.23 | 27.23 | 27.33 |
| 20 ng | 23.73 | 23.72 | 23.84 | 23.94 |
| 200 ng | 20.30 | 20.36 | 20.35 | 20.40 |
| 2 μg | 16.92 | 17.05 | 17.15 | 17.02 |

Ct Value

Example 5

Reverse Transcription Reaction-2 in the Presence of DNaseI in Reaction Composition, DNaseI Showing no Action The amount of cDNA synthesized with the reverse transcriptase in the presence of DNaseI in the reaction composition, DNaseI showing no action was compared to the amount of cDNA synthesized with a standard reverse transcription reaction composition not containing DNaseI.

A mixed solution having a total volume of 10 µL, containing 1 µL mouse liver total RNA solution serially diluted from 2 µg/µL to 20 pg/µL, component described in reaction solution 2 of Table 3 of Example 2, and 5 U DNaseI was prepared. This mixed solution was incubated at 42° C. for 2 minutes, and thereafter a solution containing 200 U PrimeScript(registered trademark) RTase (TAKARA BIO INC.), 20 U RNase Inhibitor (TAKARA BIO INC.), 100 mM Tris-HCl (pH 9.2) containing 50 pmol Oligo dT primer and 100 pmol Random 6 mers, 20 mM KCl, 20 mM DTT, 1 mM dNTP, and 28 mM $(NH_4)_2SO_4$ was added thereto in an amount of 10 µL while mixing. In other words, the above solution containing a reverse transcriptase was added to the mixed solution after the DNase treatment, so as to have final concentrations of components other than the reverse transcriptase, DNaseI, the RNase inhibitor and the primers to be those as listed in Reaction Solution 5 of Table 3 of Example 2. Next, a reverse transcription reaction was carried out under the conditions of 37° C. for 15 minutes, and thereafter the reverse transcriptase was deactivated under the conditions of 85° C. for 5 seconds.

On the other hand, a standard reverse transcription reaction composition not containing DNaseI was a reaction solution having a total volume of 10 µL, containing 1 µL of mouse liver total RNA solution serially diluted from 2 µg/µL to 20 µg/µL, 200 U PrimeScript(registered trademark) RTase (TAKARA BIO INC.), 20 U RNase Inhibitor (TAKARA BIO INC.), 50 pmol Oligo dT primer, and 100 pmol Random 6 mers, 50 mM Tris-HCl (pH 8.3), 75 mM KCl, and 3 mM $MgCl_2$ was prepared. Using this reaction solution, a reverse transcription reaction was carried out under the conditions of 37° C. for 15 minutes, and thereafter the reverse transcriptase was deactivated under the conditions of 85° C. for 5 seconds.

The amount of cDNA synthesized after the reverse transcription reaction was evaluated with the real-time PCR in which Rsp18 gene region was used as a targeting sequence. Here, in the real-time PCR, SYBR Premix ExTaq (Perfect Real Time, TAKARA BIO INC.) was used, and a primer consisting of the nucleotide sequence as shown in SEQ ID NO: 1 of Sequence Listing and a primer consisting of the nucleotide sequence as shown in SEQ ID NO: 2 of Sequence Listing were used as a primer pair.

The results of the real-time PCR are shown in Table 5. As shown in Table 5, the Ct values obtained by real-time RT-PCR according to the method of the present invention were nearly agreed with the Ct values obtained by conventional, standard real time RT-PCR. It was clarified from the above that the method of the present invention is capable of efficiently carrying out a reverse transcription reaction while completely inhibiting degradation of cDNA synthesis product with DNaseI.

TABLE 5

| RNA/20 µL Reaction Solution | Standard Reaction | Reaction Solution 5 |
| --- | --- | --- |
| NTC | — | — |
| 20 pg | 35.04 | 35.15 |
| 200 pg | 31.94 | 31.71 |
| 2 ng | 28.34 | 28.00 |
| 20 ng | 24.78 | 24.59 |
| 200 ng | 21.55 | 21.29 |
| 2 µg | 18.01 | 18.09 |

Ct Value

Example 6

Reverse Transcription Reaction-3 in the Presence of DNaseI in Reaction Composition, DNaseI Showing no Action The amount of cDNA synthesized obtained by the method for synthesizing cDNA of the present invention was compared with the amount cDNA synthesized obtained according to a conventional method for synthesizing cDNA including degrading DNA in a sample with DNaseI, and thereafter thermally deactivating DNaseI.

A mixed solution having a total volume of 10 µL, containing 1 µL mouse liver total RNA solution serially diluted from 2 µg/µL to 20 pg/µL, the components as listed in Reaction Solution 2 of Table 3. of Example 2, and 5 U DNaseI was prepared. This mixed solution was incubated at 42° C. for 2 minutes, and thereafter a solution containing 200 U PrimeScript(registered trademark) RTase (TAKARA BIO INC.), 20 U RNase Inhibitor (TAKARA BIO INC.), 100 mM Tris-HCl (pH 9.2) containing 50 pmol Oligo dT primer and 100 pmol Random 6 mers, 20 mM KCl, 20 mM DTT, 1 mM dNTP, and 28 mM $(NH_4)_2SO_4$ was added thereto in an amount of 10 µL while mixing. In other words, the above solution containing a reverse transcriptase was added to the mixed solution after the DNase treatment, so as to have final concentrations of components other than the reverse transcriptase, DNaseI, the RNase inhibitor and the primers to be those components as listed in Reaction Solution 5 of Table 3 of Example 2. Next, a reverse transcription reaction was carried out under the conditions of 37° C. for 15 minutes, and thereafter the reverse transcriptase was deactivated under the conditions of 85° C. for 5 seconds.

On the other hand, in a conventional method for synthesizing cDNA in which DNaseI was thermally deactivated, a mixed solution having a total volume of 10 µL, containing 1 µL of a mouse liver total RNA solution serially diluted from 2 µ/µL to 20 pg/µL, the components as listed in Reaction Solution 1 of Table 3 of Example 2, and 5 U DNaseI was prepared, and the mixed solution was incubated at 42° C. for 2 minutes and thereafter incubated at 95° C. for 10 minutes, to thermally deactivate DNaseI. A solution containing 200 U PrimeScript(registered trademark) RTase (TAKARA BIO INC.), 20 U RNase Inhibitor (TAKARA BIO INC.), 50 pmol Oligo dT primer, 100 pmol Random 6 mers, 100 mM Tris-HCl (pH 8.3), 300 mM KCl, 12 mM $MgCl_2$, and 1 mM dNTP was added thereto in an amount of 10 µL while mixing. In other words, the above solution containing a reverse transcriptase was added to the mixed solution after the DNase treatment and the thermal deactivation treatment of DNase, to provide a composition having a standard reverse transcription reaction composition. Next, a reverse transcription reaction was carried out under the conditions of 37° C. for 15 minutes, and thereafter the reverse transcriptase was deactivated under the conditions of 85° C. for 5 seconds.

The amount of cDNA synthesized after the reverse transcription reaction was evaluated by real-time PCR, in which Rsp18 gene region was used as a targeting sequence. Here, in the real-time PCR, SYBR Premix ExTaq (Perfect Real Time, TAKARA BIO INC.) was used, and a primer consisting of the nucleotide sequence as shown in SEQ ID NO: 1 of Sequence Listing and a primer consisting of the nucleotide sequence as shown in SEQ ID NO: 2 of Sequence Listing were used as a primer pair.

The results of the real-time PCR are shown in Table 6. As shown in Table 6, the Ct values in a case where the cDNA obtained by the conventional method for synthesizing cDNA including degrading DNA in a sample, and thereafter thermally deactivating DNaseI was used as a template are found to be delayed in two cycles or so, as compared to the Ct values obtained by the real time RT-PCR according to the method of the present invention. It is considered that this delay is caused by the degradation of RNA that serves as a template of cDNA synthesis upon the thermal deactivation of DNaseI. The present Example shows usefulness of the method for synthesizing cDNA of the present invention in which thermal deactivation of DNaseI is not needed.

TABLE 6

| RNA/20 μL Reaction Solution | Standard Reaction | Reaction Solution 5 |
|---|---|---|
| NTC | — | — |
| 20 pg | 38.19 | 35.45 |
| 200 pg | 33.69 | 31.88 |
| 2 ng | 30.24 | 28.20 |
| 20 ng | 26.57 | 24.54 |
| 200 ng | 23.22 | 21.30 |
| 2 μg | 19.98 | 17.80 |

Ct Value

Example 7

Degradation of Genomic DNA in the Method of the Present Invention

Degradation of DNA in a sample by carrying out the method for synthesizing cDNA of the present invention was confirmed by the following method.

Firstly, a mixed solution having a total volume of 10 μL, containing 1 μL of 200 ng/μL mouse genomic DNA solution, 10 U RNase Inhibitor (TAKARA BIO INC.), the components as listed in Reaction Solution 2 of Table 3, and 5 U DNaseI was prepared. In addition, 10 μL of a mixed solution having the same composition as mentioned above except that DNaseI was not contained was prepared. These mixed solutions were incubated at 42° C. for 2 minutes, and thereafter a solution containing 20 U RNase Inhibitor (TAKARA BIO INC.), 100 mM Tris-HCl (pH 9.2) containing 50 pmol Oligo dT primer and 100 pmol Random 6 mers, 20 mM KCl, 20 mM DTT, 1 mM dNTP, and 28 mM $(NH_4)_2SO_4$ was added thereto in an amount of 10 μL while mixing. In other words, the above solution was added to the mixed solution after the DNase treatment, so as to have final concentrations of components other than DNaseI, the RNase inhibitor and the primers to be those components as listed in Reaction Solution 5 of Table 3. Next, a reaction was carried out at 37° C. for 15 minutes and then at 85° C. for 5 seconds. The amount of the mouse genomic DNA remaining after the reaction was evaluated by 40 cycles of real-time PCR in which Rsp18 gene region was used as a targeting sequence. Here, in the real-time PCR, SYBR Premix ExTaq (Perfect Real Time, TAKARA BIO INC.) was used, and a primer consisting of the nucleotide sequence as shown in SEQ ID NO: 1 of Sequence Listing and a primer consisting of the nucleotide sequence as shown in SEQ ID NO: 2 of Sequence Listing were used as a primer pair.

As a result of the real-time PCR, the Ct values in a case where a mixed solution not containing DNaseI was used was 22.68, while an amplified product could not be confirmed at all in a case where a mixed solution containing DNaseI was used. It was confirmed from the results that the method for synthesizing cDNA of the present invention is capable of avoiding the production of an amplified product derived from DNA contaminated in the sample.

Example 8

Efficiency of cDNA Synthesis According to the Method of the Present Invention

The efficiency of cDNA synthesis according to the method of the present invention was compared with the efficiency of cDNA synthesis according to the method of simultaneous actions with DNaseI and a reverse transcriptase.

(1) Template RNA

As a template, a mouse liver total RNA solution serially diluted from 2 μg/μL to 20 pg/μL, in which genomic DNA was removed and purified according to a standard protocol of a total RNA extraction kit NucleoSpin(registered trademark) RNA II (MACHEREY-NAGEL GmbH & Co. KG) was used.

(2) cDNA Synthesis According to Method of Actions with DNaseI and Reverse Transcriptase at the Same Time A mixed solution having a total volume of 20 μL, containing 1 μL of the above template RNA solution, the components as listed in Reaction Solution 1 of Table 3 of Example 2, 0.5 mM dNTP, 200 U PrimeScript(registered trademark) RTase (TAKARA BIO INC.), 20 U RNase Inhibitor (TAKARA BIO INC.), 50 pmol Oligo dT primer, 100 pmol Random 6 mers, and 5 U DNaseI was prepared, of which template RNA had different concentrations in each mixed solution, a total of six kinds. In addition, a mixed solution prepared by adding 1 μL of sterile distilled water in place of the template RNA solution was prepared. As a control, a 20 μL-mixed solution having the same composition as above except that DNaseI was not contained was also prepared. For each of the mixed solution thus prepared, a reverse transcription reaction was carried out under the conditions of 37° C. for 15 minutes, and thereafter the reverse transcriptase was deactivated under the conditions of 85° C. for 5 seconds.

(3) cDNA Synthesis According to the Method of the Present Invention

A mixed solution having a total volume of 10 μL, containing 1 μL of the template RNA solution as described in the above (1), the components as listed in Reaction Solution 2 of Table 3 of Example 2, and 5 U DNaseI was prepared, of which template RNA had different concentrations in each mixed solution, a total of six kinds. In addition, a mixture solution prepared by adding 1 μL, of sterile distilled water in place of the template RNA solution was prepared. As a control, a 10 μL-mixed solution having the same composition as above except that DNaseI was not contained was also prepared. The mixed solution thus prepared was incubated at 42° C. for 2 minutes, and thereafter a 10 μL-solution containing 200 U PrimeScript(registered trademark) RTase (TAKARA BIO INC.), 20 U RNase Inhibitor (TAKARA BIO INC.), 100 mM Tris-HCl (pH 9.2) containing 50 pmol Oligo dT primer and 100 pmol Random 6 mers, 20 mM KCl, 20 mM DTT, 1 mM dNTP, and 28 mM $(NH_4)_2SO_4$ was added thereto while mixing. In other words, the above solution containing a reverse transcriptase was added to the mixed solution after the DNase treatment, so as to have final concentrations of components other than the reverse transcriptase, DNaseI, the RNase inhibitor and the primers to be those components as listed in Reaction Solution 5 of Table 3 of Example 2 (final volume of the reaction solution: 20 μL). Next, a reverse transcription reaction was carried out at 37° C. for 15 minutes, and thereafter the reverse transcriptase was deactivated under the conditions of 85° C. for 5 seconds.

(4) Evaluation of Amount of cDNA Synthesized with Real-Time PCR

The amounts of cDNA synthesized obtained in the above (2) and (3) were evaluated with the real-time PCR in which Rsp18 gene region was used as a targeting sequence. Here, in the-real time PCR, SYBR Premix ExTaq (Perfect Real Time, TAKARA BIO INC.) was used, and a primer consisting of the nucleotide sequence as shown in SEQ ID NO: 1 of Sequence Listing and a primer consisting of the nucleotide sequence as shown in SEQ ID NO: 2 of Sequence Listing were used as a primer pair. The results of the real-time PCR are shown in Table 7 and FIG. 2. In Table 7 and FIG. 2, "(3)" shows the results in which the amount of cDNA synthesized obtained according to the above (3) was evaluated with the real-time PCR, and "(2)" shows the results in which the amount of cDNA synthesized obtained according to the above (2) was evaluated with the real-time PCR.

TABLE 7

| RNA/20 μL Reaction | (3) | | (2) | |
|---|---|---|---|---|
| Solution | DNase (−) | DNase (+) | DNase (−) | DNase (+) |
| NTC | — | — | — | — |
| 20 pg | 33.79 | 33.57 | 35.87 | — |
| 200 pg | 30.11 | 30.09 | 31.76 | 36.74 |
| 2 ng | 26.60 | 26.30 | 27.83 | 32.41 |
| 20 ng | 22.80 | 22.63 | 23.50 | 29.21 |
| 200 ng | 19.67 | 19.63 | 19.91 | 26.48 |
| 2 μg | 15.96 | 15.91 | 16.18 | 23.21 |

Ct Value

Figure 2:
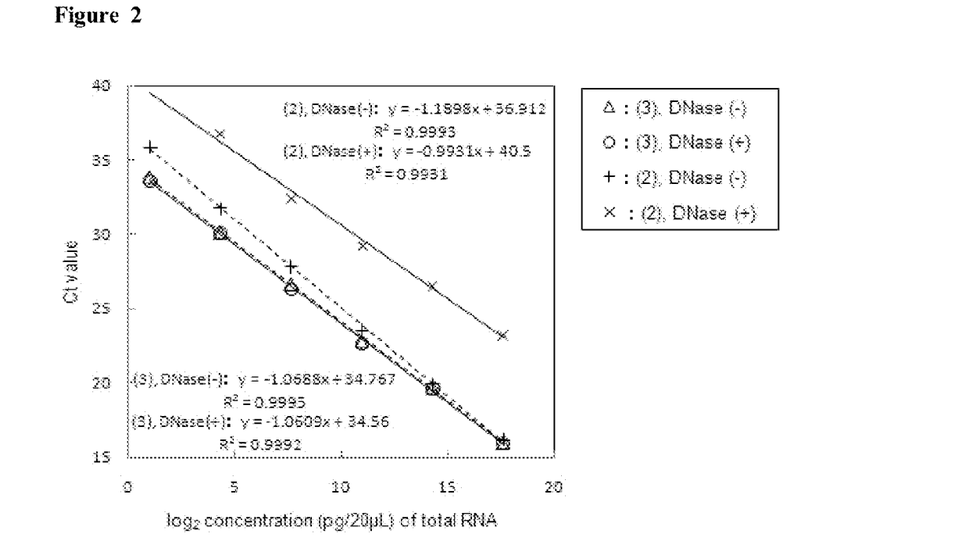
FIG. 2 is a graph showing the results of real-time PCR in Example 8.

As shown in Table 7 and FIG. 2, in the method of actions with DNaseI and a reverse transcription at the same time, in other words in DNase (+) of the method (2), the amounts of cDNA synthesized were lowered with DNase, so that the Ct values were increased. The causation therefor includes degradation of cDNA synthesized in a reverse transcription reaction with DNase. On the other hand, in the method of the present invention, an influence to cDNA synthesis with DNase was not found.

Industrial Applicability

The method and the kit for synthesizing cDNA of the present invention are widely useful in genetic engineering fields.

Sequence Listing Free Text

SEQ ID NO: 1; Primer to amplify the cDNA fragment of mouse Rsp18 gene.

SEQ ID NO: 2; Primer to amplify the cDNA fragment of mouse Rsp18 gene.

The invention claimed is:

1. A method for synthesizing cDNA which comprises the following steps (a) to (c):
   (a) obtaining a composition comprising a sample comprising RNA and DNA, and an endodeoxyribonuclease;
   (b) treating the composition obtained in step (a) under conditions sufficient to degrade the DNA; and
   (c) adding an additive comprising at least dithiothreitol and ammonium ion, and a reverse transcriptase to the composition treated in step (b) to prepare a reaction solution wherein activity of the endodeoxyribonuclease is inhibited without heat denaturation at 60° C. or higher, and carrying out a reverse transcription reaction with the reverse transcriptase to synthesize cDNA,
   wherein the concentration of dithiothreitol in the reaction solution ranges from 11 mM to 30 mM, and
   wherein the concentration of ammonium ion in the reaction solution ranges from 20 mM to 60 mM.

2. The method according to claim 1, wherein the endodeoxyribonuclease is deoxyribonuclease I.

3. The method according to claim 1, wherein the reverse transcriptase is a reverse transcriptase derived from Moloney murine leukemia virus.

4. The method according to claim 1, further comprising the step of carrying out a gene amplification reaction with the synthesized cDNA as a template.

5. The method according to claim 2, further comprising the step of carrying out a gene amplification reaction with the synthesized cDNA as a template.

6. The method according to claim 3, further comprising the step of carrying out a gene amplification reaction with the synthesized cDNA as a template.

7. The method according to claim 1, wherein the activity of the endodeoxyribonuclease is inhibited by at least 71%.

8. The method according to claim 1, wherein the concentration of dithiothreitol in the reaction solution ranges from 11.25 to 20 mM.

9. The method according to claim 8, wherein the additive further comprises a potassium ion.

10. The method according to claim 9, wherein the additive further comprises magnesium ion in a concentration of 2 mM.

11. The method according to claim 1, wherein the concentration of ammonium ion in the reaction solution ranges from 28 mM to 56 mM.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Primer to amplify the cDNA fragment of mouse
      Rsp18 gene.

<400> SEQUENCE: 1
ttctggccaa cggtctagac aac                                             23

<210> SEQ ID NO 2
<211> LENGTH: 21
<212> TYPE: DNA
<213> ORGANISM: Artificial Sequence
<220> FEATURE:
<223> OTHER INFORMATION: Primer to amplify the cDNA fragment of mouse
      Rsp18 gene.

<400> SEQUENCE: 2
ccagtggtct tggtgtgctg a                                               21
```